United States Patent [19]

Hosobuchi

[11] Patent Number: 4,459,299
[45] Date of Patent: Jul. 10, 1984

[54] REVERSAL OF ISCHEMIC NEUROLOGIC DEFICITS IN HUMANS

[75] Inventor: Yoshio Hosobuchi, San Rafael, Calif.

[73] Assignee: Regents of the University of California, Berkeley, Calif.

[21] Appl. No.: 438,811

[22] Filed: Nov. 3, 1982

[51] Int. Cl.³ .......................................... A61K 31/485
[52] U.S. Cl. .................................................... 424/260
[58] Field of Search ........................................ 424/260

[56] References Cited

PUBLICATIONS

Chem.-Abst., 10th Collective index.
Chem. Substances-Methanediamine-1-Naphthalenol, pp. 32589CS-32590CS.

Primary Examiner—Stanley J. Friedman
Attorney, Agent, or Firm—Bertram I. Rowland

[57] ABSTRACT

Methods and compositions are provided for reversing ischemic deficits in stroke victims by treating the stroke victim with an effective amount of the opiate antagonist naltrexone.

4 Claims, No Drawings

REVERSAL OF ISCHEMIC NEUROLOGIC DEFICITS IN HUMANS

BACKGROUND OF THE INVENTION

1. Field of the Invention

Stroke victims are frequently left with partial paralysis which may or may not slowly be reversed over long periods of time. The partial paralysis frequently manifests itself in difficulties in movement and speech, when the left hemisphere is involved. The mechanisms by which paralysis occurs and is resolved by natural processes is not understood. It would therefore be desirable to provide methods for alleviating stroke victims from the physical disorders as a result of ischemia.

2. Description of the Prior Art

Hosobuchi et al., Science (1982) 215:69-71 reports the use of naloxone reversed hemiplegia secondary to cerebral ischemia in two patients for up to 20 mins. and naloxone was shown to be effective in reversing induced ischemic neurologic deficit in gerbils. See also the references cited therein.

Baskin and Hosobuchi, Lancet (1981) 2:272-275 report the naloxone reversal of ischemic neurologic deficits in man.

SUMMARY OF THE INVENTION

Naltrexone is administered in sufficient amount to reverse neurological deficits in patients who have suffered stroke.

DESCRIPTION OF THE SPECIFIC EMBODIMENTS

Methods and compositions are provided for resolving significant amounts of neurological deficits in patients who have suffered stroke, even where substantial periods of time have passed since the stroke incident. The method and compositions involve the administration of naltrexone to a patient to reverse physical disabilities as a result of residual neurological deficits.

The naltrexone may be used by itself or in combination with other opiate antagonists e.g. naloxone. Normally, in a mixture, naltrexone will be used in at least 50 mg/dose, more usually at least 75 mg/dose and generally in at least 100 mg/dose. Depending upon the mold of administration, the naltrexone may be formulated with a wide variety of physiologically acceptable carriers. The formulation may be liquid or dry, using physiologically acceptable liquids, such as aqueous saline, phosphate buffered saline, etc. or a wide variety of acceptable excipients, e.g. glucose, mannitol, etc.

The dosage will generally be at least about 50 mg per day and not more than about 200 mg per day, generally being from about 75 to 150 mg per day. The dosage may be administered as a single dosage, but preferably will be administered, usually at least two and not more than about five.

Various methods of administration may be employed, but most conveniently oral administration will be used. Other techniques include intravenous, intraperitoneal, and the like. Individual dosages may include tablets, capsules, powders, solutions, etc. In some instances the naltrexone may be administered on a continuous basis, through an automatic monitoring device. Individual dosages will generally range from about 10 to 150, usually 20 to 150, and more usually 25 to 100 mg naltrexone/day.

In order to demonstrate the use of naltrexone, five patients who had suffered strokes at least two years prior to the tests were employed. Each of the patients had physical handicaps on the right side, indicating ischemic neurologic deficit in the hemisphere. Also, each of the patients had speech language disabilities.

Single blind tests were employed and the activities and speech of the patients were videotaped during and after the first month when placebos were administered and during and after the second month when the naltrexone had been administered orally at a rate of 100 mg/day—divided into two dosages—for a period of one month. The video sequences were randomized and two groups of judges employed to rate each of the sequences. The first group was composed of five experienced physical therapists who rated the physical abilities of the patients as observed in the videotaped sequences. The second group were three speech language pathologists. The ratings were scored and each patient was found to have had no improvement during the one month administration of placebos, but at least a 20% improvement at the end of the one month treatment with naltrexone. No untoward reactions were observed as a result of the naltrexone administration, there being no adverse symptoms observed.

It is evident from the above results, that ischemic neurological deficits can be reversed at least in part by repetitive administration of naltrexone over extended periods of time. By providing for tablets, capsules or solutions which can be taken by the patient at regular intervals and at carefully determined dosages, stroke victims can reduce physical disabilities by naltrexone administration.

Although the foregoing invention has been described in some detail by way of illustration and example for purposes of clarity of understanding, it will be obvious that certain changes and modifications may be practiced within the scope of the appended claims.

What is claimed is:

1. A method for reversing at least in part ischemic neurologic deficits which comprises:
    administering to a host suffering from ischemic neurologic deficits, an effective amount of naltrexone.

2. A method according to claim 1, wherein said administration is by oral means employing an orally acceptable dosage.

3. A method according to any of claim 1 about 25 to 100 mg of naltrexone in a physiologically acceptable carrier is administered in individual dosages to provide from about 50 to 200 mg daily.

4. A method according to claim 3, wherein said individual dosages are from about 10 to 100 mg naltrexone.

* * * * *